US008923974B2

(12) United States Patent
Bradley

(10) Patent No.: US 8,923,974 B2
(45) Date of Patent: Dec. 30, 2014

(54) SYSTEM AND METHOD FOR ELECTRICAL MODULATION OF THE POSTERIOR LONGITUDINAL LIGAMENT

(75) Inventor: Kerry Bradley, Glendale, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 40 days.

(21) Appl. No.: 13/469,880

(22) Filed: May 11, 2012

(65) Prior Publication Data

US 2012/0290059 A1 Nov. 15, 2012

Related U.S. Application Data

(60) Provisional application No. 61/486,157, filed on May 13, 2011.

(51) Int. Cl.
*A61N 1/00* (2006.01)
*A61N 1/05* (2006.01)
*A61N 1/36* (2006.01)

(52) U.S. Cl.
CPC .......... *A61N 1/0551* (2013.01); *A61N 1/36071* (2013.01)
USPC ....................................................... 607/46

(58) Field of Classification Search
CPC . A61N 1/3605; A61N 1/0551; A61N 1/0553; A61N 1/05531
USPC .................................................. 607/46, 117
See application file for complete search history.

(56) References Cited

U.S. PATENT DOCUMENTS

| 6,895,280 | B2 | 5/2005 | Meadows et al. | |
|---|---|---|---|---|
| 7,069,083 | B2 | 6/2006 | Finch et al. | |
| 7,529,582 | B1 * | 5/2009 | DiLorenzo | 607/2 |
| 8,452,417 | B2 * | 5/2013 | Navarro | 607/117 |
| 2006/0241716 | A1 * | 10/2006 | Finch et al. | 607/43 |
| 2008/0004674 | A1 * | 1/2008 | King et al. | 607/46 |
| 2012/0165898 | A1 | 6/2012 | Moffitt | |
| 2012/0215218 | A1 * | 8/2012 | Lipani | 606/41 |

OTHER PUBLICATIONS

U.S. Appl. No. 61/463,800, filed Feb. 23, 2011.*
U.S. Appl. No. 61/427,441, Title: Neurostimulation System for Selectively Estimating Volume of Activation and Providing Therapy, Inventor: Michael A. Moffitt, filed Dec. 27, 2010.
Groen, Gerbrand J. et al., Nerves and Nerve Plexuses of the Human Vertebral Column, The American Journal of Anatomy, 188: 282-296 (1990).
Bogduk, Nikolai, The Innervation of the Lumbar Spine, Spine 1983; 8(3).

* cited by examiner

*Primary Examiner* — Scott Getzow
(74) *Attorney, Agent, or Firm* — Vista IP Law Group LLP

(57) ABSTRACT

A method for treating a patient having discogenic pain includes implanting a neurostimulation lead within an anterior portion of the epidural space adjacent to the posterior longitudinal ligament. A plurality of electrodes is attached to the lead and the lead is implanted with at least a portion of the electrodes facing the posterior longitudinal ligament. The lead may be implanted in the lumbar region of the patient's spine, posterior and parallel to the posterior longitudinal ligament. Electrical stimulation energy applied to the patient through the electrode lead implanted in this manner inhibits the pain signals traveling within the posterior longitudinal ligament. Thus, the applied electrical stimulation energy has an anesthetic effect on the pain fibers adjacent to the posterior longitudinal ligament.

4 Claims, 5 Drawing Sheets

SYSTEM AND METHOD FOR ELECTRICAL MODULATION OF THE POSTERIOR LONGITUDINAL LIGAMENT

RELATED APPLICATION DATA

The present application claims the benefit under 35 U.S.C. §119 to U.S. provisional patent application Ser. No. 61/486,157, filed May 13, 2011. The foregoing application is hereby incorporated by reference into the present application in its entirety.

FIELD OF THE INVENTION

The present inventions relate to systems and methods for electrical modulation of the posterior longitudinal ligament during spinal cord stimulation.

BACKGROUND OF THE INVENTION

Implantable neurostimulation systems have proven therapeutic in a wide variety of diseases and disorders. For example, Spinal Cord Stimulation (SCS) techniques, which directly stimulate the spinal cord tissue of the patient, have long been accepted as a therapeutic modality for the treatment of chronic pain syndromes, and the application of spinal cord stimulation has expanded to additional applications, such as angina pectoralis, peripheral vascular disease, and incontinence, among others.

An implantable SCS system typically includes one or more electrode-carrying stimulation leads, which are implanted at a stimulation site in proximity to the spinal cord tissue of the patient, and a neurostimulator implanted remotely from the stimulation site, but coupled either directly to the stimulation lead(s) or indirectly to the stimulation lead(s) via a lead extension. The neurostimulation system may further comprise a handheld patient programmer to remotely instruct the neurostimulator to generate electrical stimulation pulses in accordance with selected stimulation parameters. The handheld programmer may, itself, be programmed by a technician attending the patient, for example, by using a Clinician's Programmer (CP), which typically includes a general purpose computer, such as a laptop, with a programming software package installed thereon.

Thus, programmed electrical pulses can be delivered from the neurostimulator to the stimulation lead(s) to stimulate or activate a volume of the spinal cord tissue. In particular, electrical stimulation energy conveyed to the electrodes creates an electrical field, which when strong enough, depolarizes (or "stimulates") the neural fibers within the spinal cord beyond a threshold level, thereby inducing the firing of action potentials (APs) that propagate along the neural fibers to provide the desired efficacious therapy to the patient.

Spinal cord stimulation is an application of the "gate control theory," which theorizes that painful stimuli can be modulated by touch and vibratory sensations. Nociceptive information (i.e., related to painful stimuli) is carried by small nerve fibers, while innocuous (e.g., touch, vibration, pressure) information is carried by large nerve fibers, both of which interact within the dorsal horn of the spinal cord (the ostensible location of the "the gate"). The gate control theory suggests that activation of large nerve fibers carrying touch and vibratory sensation may be manipulated to "close the gate" to the small nerve fibers carrying painful peripheral stimuli. As such, spinal cord stimulation acts as an analgesic, relieving pain by stimulating the branches of the large nerve fibers in the dorsal columns, which then deliver action potentials to the dorsal horn, thereby counteracting the painful stimuli carried by corresponding small nerve fibers. In order for spinal cord stimulation to function effectively, the stimulation must be applied to the appropriate large nerve fibers that correspond to the small nerve fibers carrying the painful stimuli. That is, the applied stimulation must be carefully mapped to the painful body area. Programming and mapping procedures have been developed in order to ensure that the appropriate large nerve fibers are stimulated during SCS to provide effective treatment of pain.

Discogenic back pain is believed to be nociceptive in nature. With intervertebral disc degeneration, increased nerve fiber growth into the outer annulus of the intervertebral disc is observed, and these fibers can become sensitized and thus hyperactive. These nerve fibers are believed to be pain-carrying afferents traveling within the sinuvertebral nerves, which run within or around the posterior longitudinal ligament of the spine near the affected levels of the degenerating discs. SCS has been shown to provide some pain relief in patients with discogenic pain, though the exact mechanism of relief is not known.

However, while SCS techniques may blunt the pain, they typically do not block the pain sensation altogether. There, thus, remains a need for a SCS technique that provides direct inhibition of the pain signals from the degenerated intervertebral discs.

SUMMARY OF THE INVENTION

In accordance with a first aspect of the present inventions, a method for treating a patient having a spine comprising an epidural space and a posterior longitudinal ligament is provided. The method includes implanting a neurostimulation lead within an anterior portion of the epidural space adjacent to the posterior longitudinal ligament. The neurostimulation lead may include plurality of electrodes, and at least portions of the electrodes may face the posterior longitudinal ligament. The neurostimulation lead may be implanted parallel and/or posterior to the posterior longitudinal ligament, and may be implanted within a lumbar region of the patient's spine. The neurostimulation lead may be a paddle lead and the plurality of electrodes may be disposed on the same side of the paddle lead. The paddle lead may be implanted such that the electrodes face the posterior longitudinal ligament. Alternatively, the neurostimulation lead may be a cylindrical lead and the electrodes may be radially segmented electrodes. The electrode segments facing the posterior longitudinal ligament may be chosen to be active.

In accordance with a second aspect of the present inventions, a method for providing therapy to a patient implanted with a plurality of electrodes within an anterior portion of an epidural space adjacent to the posterior longitudinal ligament is provided. The method includes applying electrical stimulation energy to the patient through the electrodes, wherein the applied electrical stimulation energy inhibits pain signals traveling within the posterior longitudinal ligament. The applied electrical stimulation energy thus may have some anesthetic effect on pain fibers adjacent to the posterior longitudinal ligament. The plurality of electrodes may be implanted within a lumbar region of the patient's spine.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

The description that follows relates to a spinal cord stimulation (SCS) system. However, it is to be understood that the while the invention lends itself well to applications in SCS, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neural stimulator configured to treat urinary incontinence, sleep apnea, shoulder sublaxation, headache, etc.

Figure 1:
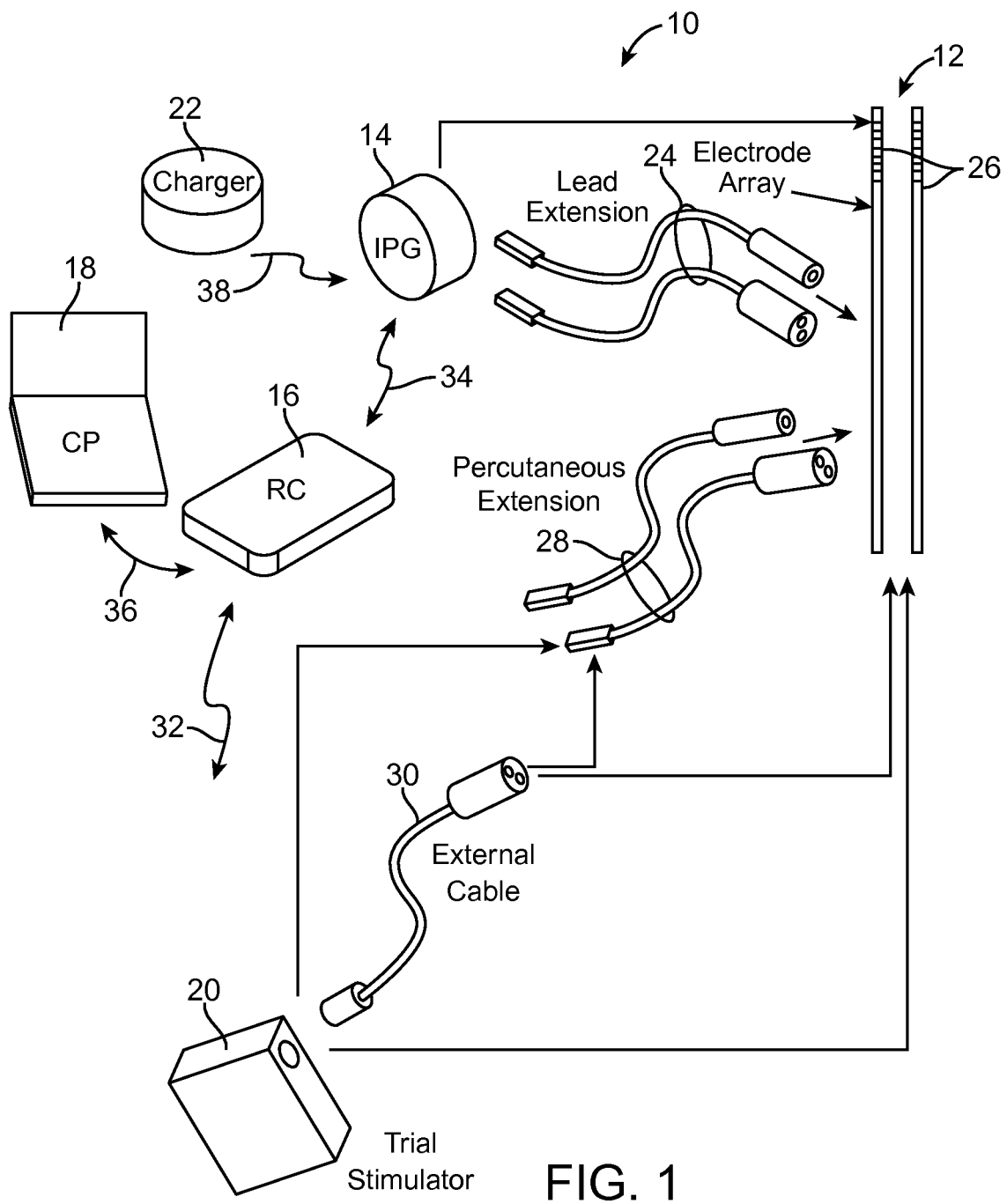
FIG. 1 is a plan view of an embodiment of a spinal cord stimulation (SCS) system arranged in accordance with the present inventions.

Turning first to FIG. 1, an exemplary SCS system 10 generally includes one or more (in this case, two) implantable stimulation leads 12, an implantable pulse source (IPG) 14, an external remote controller RC 16, a clinician's programmer (CP) 18, an External Trial Stimulator (ETS) 20, and an external charger 22.

The IPG 14 is physically connected via one or more percutaneous lead extensions 24 to the stimulation leads 12, which carry a plurality of electrodes 26 arranged in an array. In the illustrated embodiment, the stimulation leads 12 are percutaneous leads, and to this end, the electrodes 26 are arranged in-line along the stimulation leads 12. In alternative embodiments, the electrodes 26 may be arranged in a two-dimensional pattern on a single paddle lead. As will be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters.

The ETS 20 may also be physically connected via the percutaneous lead extensions 28 and external cable 30 to the stimulation leads 12. The ETS 20, which has similar pulse generation circuitry as that of the IPG 14, also delivers electrical stimulation energy in the form of a pulsed electrical waveform to the electrode array 26 in accordance with a set of stimulation parameters. The major difference between the ETS 20 and the IPG 14 is that the ETS 20 is a non-implantable device that is used on a trial basis after the stimulation leads 12 have been implanted and prior to implantation of the IPG 14, to test the responsiveness of the stimulation that is to be provided.

The RC 16 may be used to telemetrically control the ETS 20 via a bi-directional RF communications link 32. Once the IPG 14 and stimulation leads 12 are implanted, the RC 16 may be used to telemetrically control the IPG 14 via a bi-directional RF communications link 34. Such control allows the IPG 14 to be turned on or off and to be programmed with different stimulation parameter sets. The IPG 14 may also be operated to modify the programmed stimulation parameters to actively control the characteristics of the electrical stimulation energy output by the IPG 14.

The CP 18 provides clinician detailed stimulation parameters for programming the IPG 14 and ETS 20 in the operating room and in follow-up sessions. The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown). The clinician detailed stimulation parameters provided by the CP 18 are also used to program the RC 16, so that the stimulation parameters can be subsequently modified by operation of the RC 16 in a stand-alone mode (i.e., without the assistance of the CP 18). The external charger 22 is a portable device used to transcutaneously charge the IPG 14 via an inductive link 38. Once the IPG 14 has been programmed, and its power source has been charged by the external charger 22 or otherwise replenished, the IPG 14 may function as programmed without the RC 16 or CP 18 being present.

For purposes of brevity, the details of the RC 16, CP 18, ETS 20, and external charger 22 will not be described herein. Details of exemplary embodiments of these devices are disclosed in U.S. Pat. No. 6,895,280, which is expressly incorporated herein by reference.

Figure 2:
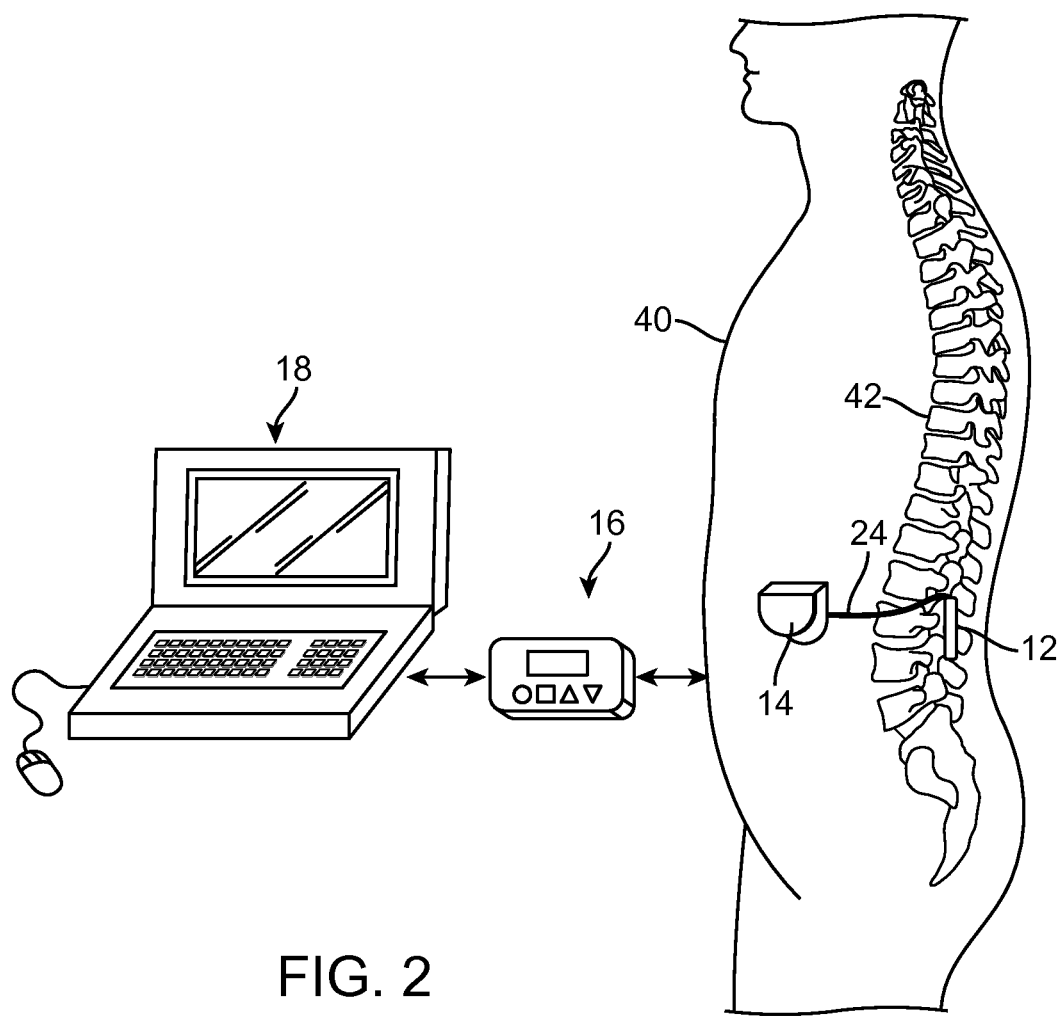
FIG. 2 is a plan view of the SCS system of FIG. 1 in use within a patient.

As shown in FIG. 2, the electrode leads 12 are implanted within the spinal column 42 of a patient 40. Due to the lack of space near the location where the electrode leads 12 exit the spinal column 42, the IPG 14 is generally implanted in a surgically-made pocket either in the abdomen or above the buttocks. The IPG 14 may, of course, also be implanted in other locations of the patient's body. The lead extension 24 facilitates locating the IPG 14 away from the exit point of the electrode leads 12. As there shown, the CP 18 communicates with the IPG 14 via the RC 16.

In a conventional SCS system, the electrode leads are placed within the thoracic region of the spinal column. However, in accordance with the present invention, and as shown in FIG. 2, the electrode leads 12 of the SCS system may be implanted within the lumbar region of the spinal column 42 adjacent to the diseased discs, which are the source of the patient's discogenic pain. Additionally or alternatively, electrode leads 12 may be implanted in other regions of the spinal column 42 to target different vertebral levels. For example, if the diseased discs are located in the thoracic or cervical spinal regions, the electrode leads 12 are implanted in the thoracic or cervical spinal regions adjacent to the diseased discs.

Figure 4:
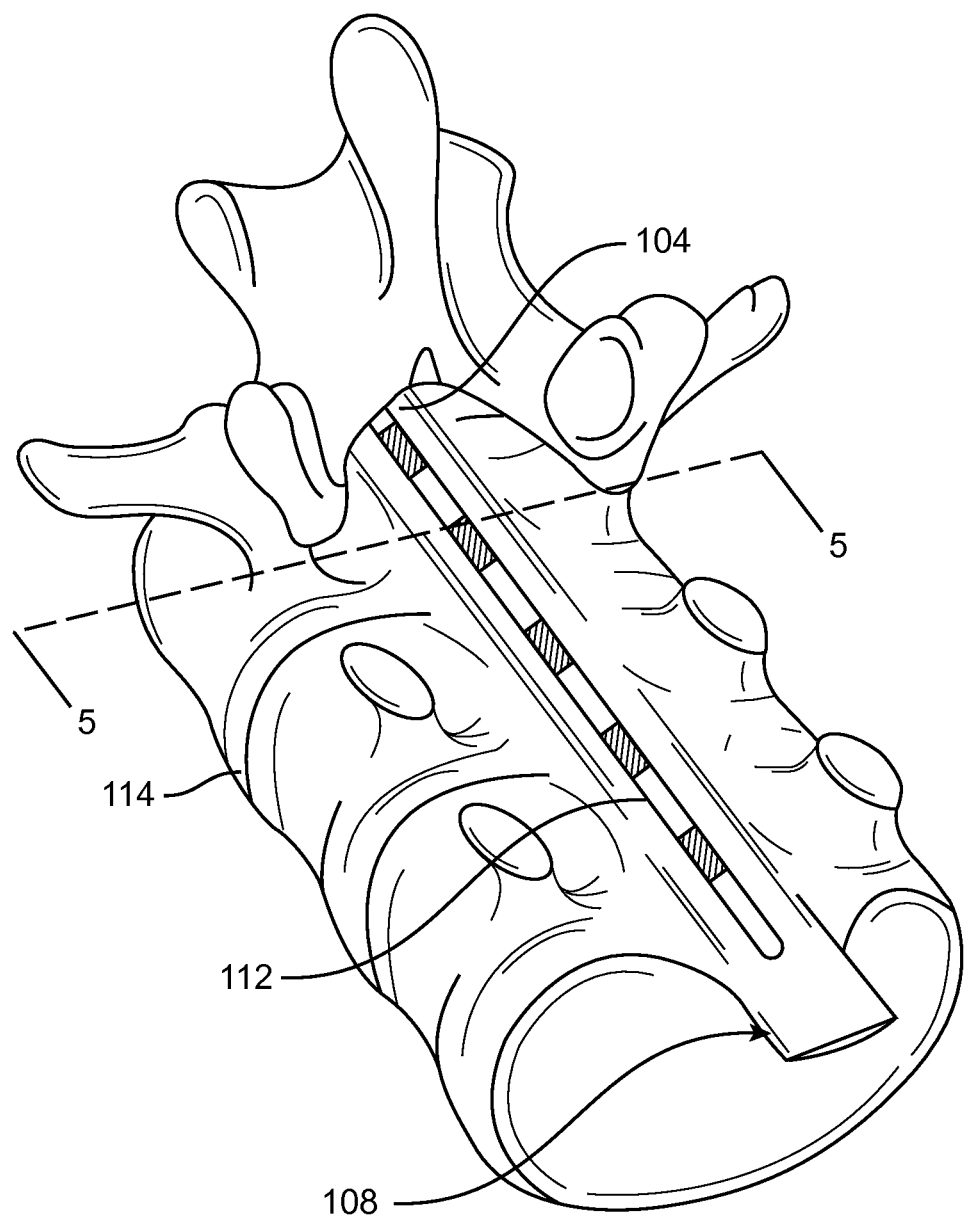
FIG. 4 is a perspective, partial cut-away view of a portion of a spinal column, depicting a position of a lead used in the SCS system of FIG. 1.
Figure 5:
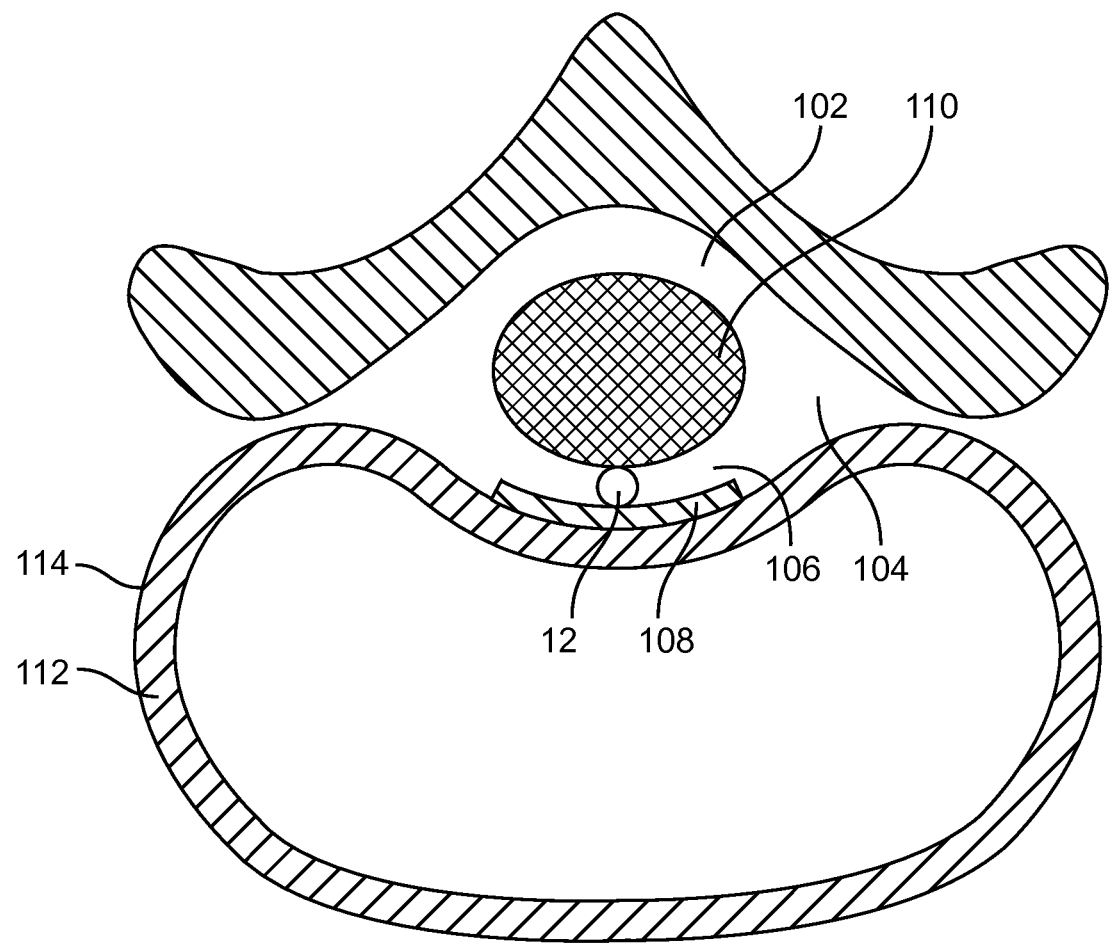
FIG. 5 is a cross-sectional view of the spinal column taken along the line 5-5 in FIG. 4.

Because the pain fibers in the diseased discs are very small, they are difficult to manipulate directly with electrical energy. Thus, as shown in FIGS. 4 and 5 and discussed in greater detail below, the electrode leads 12 are positioned such that electrical stimulation energy is applied to nerves in the posterior longitudinal ligament 108, which is attached to the outer fibers of the annulus 112 of the intervertebral discs 114. Applying electrical stimulation energy to the posterior longitudinal ligament 108 in accordance with the present invention may have an anesthetic effect on the pain-carrying fibers from the intervertebral discs 114.

In particular, in accordance with the present invention, the electrode leads 12 are implanted within the anterior region 106 of the epidural space 104. The posterior longitudinal ligament 108 lines the vertebral body and is positioned between the spinal cord 110 (shown in FIG. 5) and the annulus 112 of the intervertebral discs 114. The leads 12 are implanted adjacent to the posterior longitudinal ligament 108. In particular, the leads 12 may be positioned posterior and parallel to the posterior longitudinal ligament 108. In contrast, in conventional SCS, the electrode leads are implanted within a dorsal region 102 of the epidural space 104.

With the electrode leads 12 positioned as described above, electrical stimulation energy applied through the electrode leads 12 creates direct inhibition of the pain signals such that the patient receives relief of pain. This is advantageous over conventional SCS methods, which rely on the gate control theory to mediate pain, but do not block the pain entirely. That is, with conventional SCS methods, pain signals are not inhibited, but rather, are dulled by applying stimulation to the large nerve fibers that correspond to the small nerve fibers carrying the pain signals. Because the SCS methods and systems of the present invention do not rely on the gate control theory, tedious mapping and programming procedures may be avoided, and reliance on the patient's neural state and possible long-term accommodation within the "gate" are minimized.

A method of treating a patient includes applying electrical stimulation energy to the patient through the electrodes, wherein the applied electrical stimulation energy provides direct inhibition of the pain signals within the posterior longitudinal ligament 108 such that the patient receives relief of pain. In this manner, the applied electrical stimulation energy has some anesthetic effect on the pain fibers.

Figure 3:
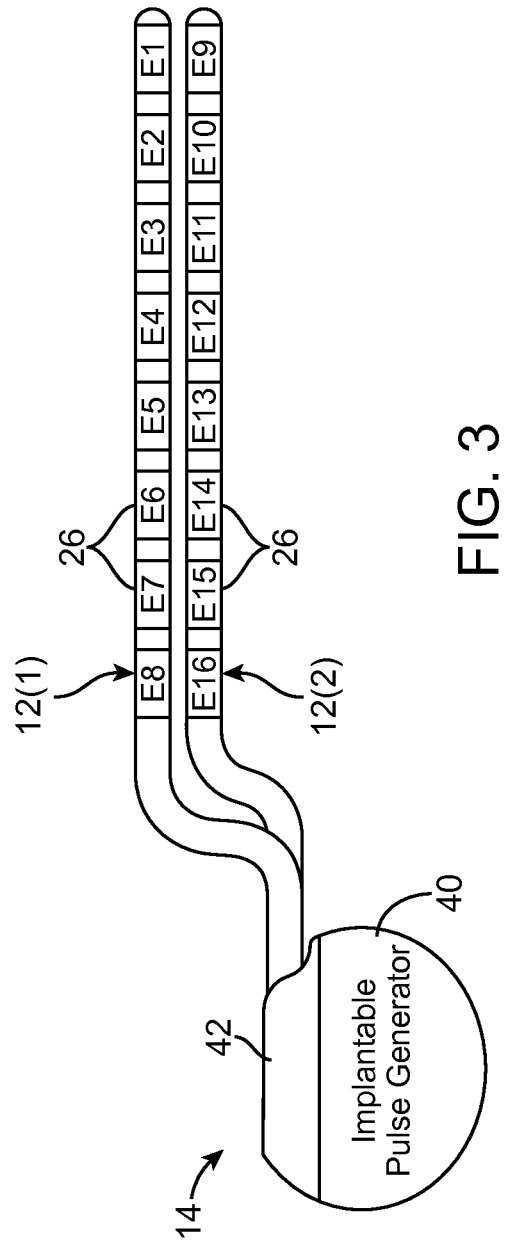
FIG. 3 is a profile view of an implantable pulse source (IPG) used in the SCS system of FIG. 1.

Referring now to FIG. 3, the external features of the stimulation leads 12 and the IPG 14 will be briefly described. One of the stimulation leads 12(1) has eight electrodes 26 (labeled E1-E8), and the other stimulation lead 12(2) has eight electrodes 26 (labeled E9-E16). The actual number and shape of leads and electrodes will, of course, vary according to the intended application.

The electrodes 26 and leads 12 are arranged such that, when implanted, at least portions of the electrodes 26 face the posterior longitudinal ligament 108. For example, the lead 12 may be a paddle lead and all of the electrodes 26 may be disposed on the same side of the paddle lead. The paddle lead may be implanted with the electrodes disposed on one side of the paddle lead facing the posterior longitudinal ligament 108. In another example, the lead may be cylindrical and the electrodes may be radially segmented electrodes. In this example, the electrode segments facing the posterior longitudinal ligament 108 may be chosen to be active. More details regarding segmented circumferential electrodes and manipulating the electrical stimulation field conveyed by such electrodes may be found, for example, in Provisional U.S. patent application Ser. No. 61/427,441, expressly incorporated herein by reference. In still another example, the electrodes may be ring electrodes, and the electrical stimulation energy may be applied such that the electrical stimulation field is focused towards the posterior longitudinal ligament 108. For example, narrow bipoles or guarded cathodes could be utilized to confine the modulating current very close to the active electrodes and focus the stimulation field.

Referring again to FIG. 3, the IPG 14 comprises an outer case 40 for housing the electronic and other components, and a connector 42 to which the proximal ends of the stimulation leads 12(1) and 12(2) mate in a manner that electrically couples the electrodes 26 to the electronics within the outer case 40. The outer case 40 is composed of an electrically conductive, biocompatible material, such as titanium, and forms a hermetically sealed compartment wherein the internal electronics are protected from the body tissue and fluids. In some cases, the outer case 40 may serve as an electrode.

The IPG 14 includes pulse generation circuitry that provides electrical conditioning and stimulation energy in the form of a pulsed electrical waveform to the electrode array 26 in accordance with a set of stimulation parameters programmed into the IPG 14. Such stimulation parameters may comprise electrode combinations, which define the electrodes that are activated as anodes (positive), cathodes (negative), and turned off (zero), percentage of stimulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse width (measured in microseconds), pulse rate (measured in pulses per second), and burst rate (measured as the stimulation on duration X and stimulation off duration Y).

Electrical stimulation will occur between two (or more) activated electrodes, one of which may be the IPG case 40. Simulation energy may be transmitted to the tissue in a monopolar or multipolar (e.g., bipolar, tripolar, etc.) fashion. Monopolar stimulation occurs when a selected one of the lead electrodes 26 is activated along with the case 40 of the IPG 14, so that stimulation energy is transmitted between the selected electrode 26 and case 40. Bipolar stimulation occurs when two of the lead electrodes 26 are activated as anode and cathode, so that stimulation energy is transmitted between the selected electrodes 26. For example, an electrode on one lead 12 may be activated as an anode at the same time that an electrode on the same lead or another lead 12 is activated as a cathode. Tripolar stimulation occurs when three of the lead electrodes 26 are activated, two as anodes and the remaining one as a cathode, or two as cathodes and the remaining one as an anode. For example, two electrodes on one lead 12 may be activated as anodes at the same time that an electrode on another lead 12 is activated as a cathode.

The stimulation energy may be delivered between electrodes as monophasic electrical energy or multiphasic electrical energy. Monophasic electrical energy includes a series of pulses that are either all positive (anodic) or all negative (cathodic). Multiphasic electrical energy includes a series of pulses that alternate between positive and negative. For example, multiphasic electrical energy may include a series of biphasic pulses, with each biphasic pulse including a cathodic (negative) stimulation pulse and an anodic (positive) recharge pulse that is generated after the stimulation pulse to prevent direct current charge transfer through the tissue, thereby avoiding electrode degradation and cell trauma. That is, charge is conveyed through the electrode-tissue interface via current at an electrode during a stimulation period (the length of the stimulation pulse), and then pulled back off the electrode-tissue interface via an oppositely polarized current at the same electrode during a recharge period (the length of the recharge pulse).

The electrical stimulation energy may be applied according to one or more stimulation strategies. Exemplary stimulation strategies include very high frequency stimulation, burst mode stimulation at a frequency above 100 Hz, anodal blockade, and cathodal blockade. With the very high frequency stimulation strategy, stimulation energy is applied at a rate above 2 kHz to hold the membrane potential at a slightly depolarized state, but without appreciable action potential generation and disallowing propagation. Stimulation energy applied in a burst mode at a rate of 100 Hz or above increases the relative threshold for activation after a brief period.

Anodal blockade, via repetitive low duty-cycle positive-pulsatile hyperpolarization, blocks transmission through the nerves and requires strong types of current. Cathodal blockade, via very strong repetitive negative-pulsatile stimulation, generates action potentials but disallows their propagation away from the activation site.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A method for treating a patient having a spine comprising an epidural space and a posterior longitudinal ligament, wherein the patient has a diseased vertebral disc, wherein the method includes:

implanting a neurostimulation lead within an anterior portion of the epidural space adjacent to the posterior longitudinal ligament, wherein the neurostimulation lead has a plurality of electrodes that are adjacent the diseased vertebral disc, wherein the neurostimulation lead is a paddle lead and the plurality of electrodes are disposed on the same side of the paddle lead, and wherein the paddle lead is implanted such that the electrodes face the posterior longitudinal ligament.

2. The method of claim 1, wherein the neurostimulation lead is implanted parallel to the posterior longitudinal ligament.

3. The method of claim 1, wherein the neurostimulation lead is implanted within a lumbar region of the patient's spine, and wherein the diseased vertebral disc is in the lumbar region.

4. The method of claim 1, wherein the neurostimulation lead is implanted posterior to the posterior longitudinal ligament.

* * * * *